Figure 1:
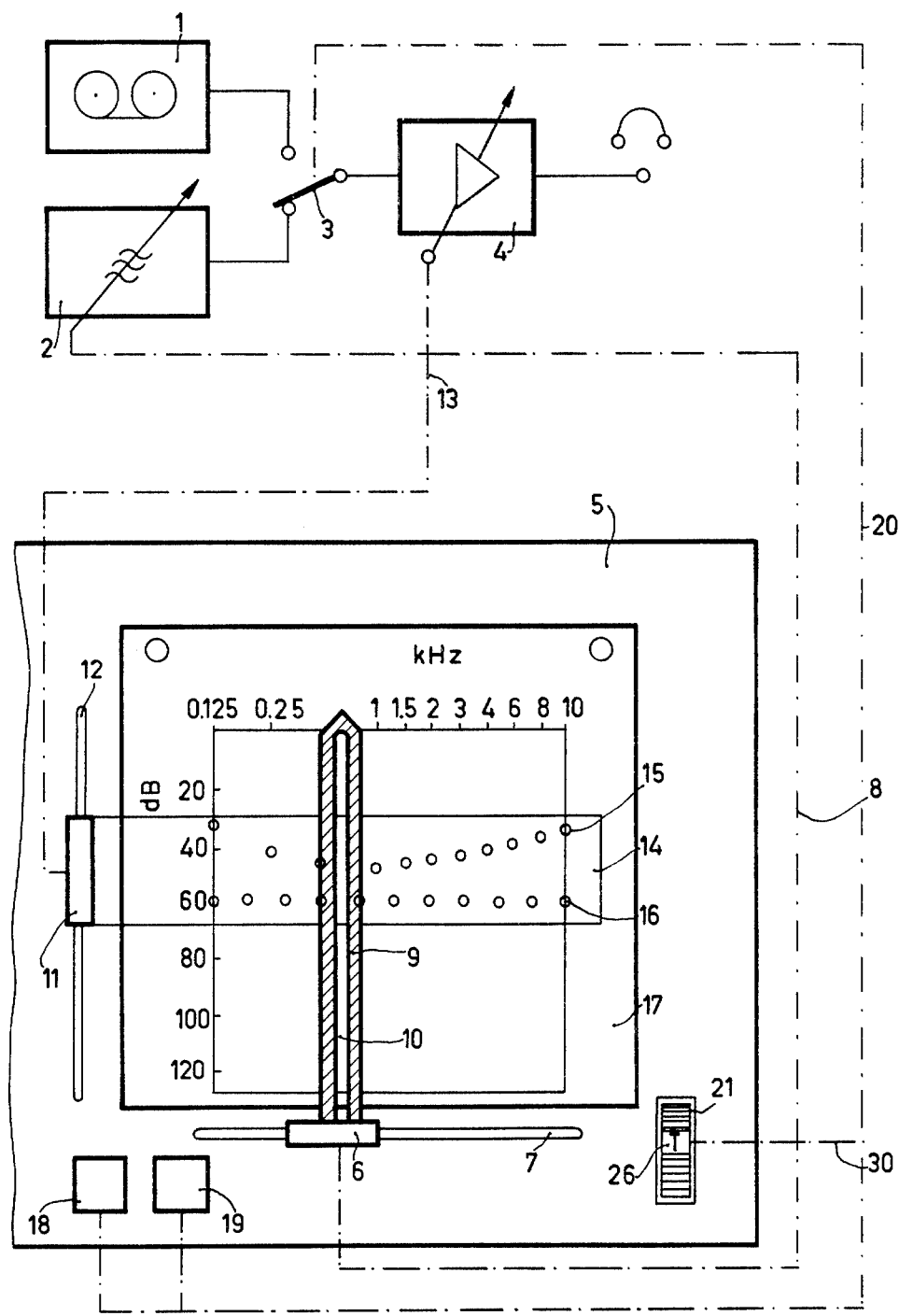

United States Patent [19]

Voss

[11] 4,109,106
[45] Aug. 22, 1978

[54] AUDIOMETER

[75] Inventor: Rainer Voss, Oststeinbek, Germany

[73] Assignee: U.S. Philips Corporation, New York, N.Y.

[21] Appl. No.: 785,876

[22] Filed: Apr. 8, 1977

[30] Foreign Application Priority Data

Apr. 10, 1976 [DE] Fed. Rep. of Germany ....... 2615903

[51] Int. Cl.² ............................................. A61B 4/07
[52] U.S. Cl. ................................................. 179/1 N
[58] Field of Search ....................... 179/1 N; 128/2 Z

[56] References Cited

U.S. PATENT DOCUMENTS 2,744,158   5/1956   Gransot ............................. 179/1 N
2,802,053   8/1957   Wiese ................................ 179/1 N

FOREIGN PATENT DOCUMENTS 915,169   9/1946   France ................................ 179/1 N Primary Examiner—Thomas W. Brown
Assistant Examiner—E. S. Kemeny
Attorney, Agent, or Firm—Frank R. Trifari; Bernard Franzblau

[57] ABSTRACT

A combined tone-speech audiometer for the semi-automatic recording of the measuring values found both in tone audiometry and in speech audiometry, the measuring point each time being defined by the point of intersection of two sliders. For tone audiometry the frequency slider is locked in locking positions which are non-equidistant, whereas for speech audiometry it is locked in positions which are equidistant. For this purpose a rotatable roller, spindle or the like is provided which has on its circumference two groups of locking positions, one for tone audiometry and one for speech audiometry. To change from one locking mode to another the spindle is rotated until the other group of locking positions is operative.

8 Claims, 2 Drawing Figures

AUDIOMETER

The invention relates to an audiometer provided with an audio-frequency tone generator whose frequency is variable in steps by means of a first slider which locks in different locking positions, and with an amplifier whose gain is variable by means of a second slider which is movable perpendicularly to the direction of movement of the first slider, a marking templet being connected to each slider which extends substantially perpendicularly to the direction of movement of this slider and parallel to the direction of movement of the other slider.

Such audiometers are known. They are employed as tone audiometers for determining the threshold of hearing at different frequencies. For this the sound level at a predetermined frequency is increased by means of the second slider until the tone is perceived by the person under observation. The point on the hearing characteristic thus determined, which is defined by the point of intersection of the two marking templets, is recorded on an audiogram chart which is fixed in a specific position underneath the marking templet by the operator inserting a dot at the intersection of the two marking templets.

In this way the hearing characteristic can be determined at twelve different frequencies (125, 250, 500 and 750 Hz, 1, 5, 2, 3, 4, 6, 8 and 12 kHz). The frequency spectrum on the audiogram chart on which the hearing characteristic is recorded has a logarithmic scale, i.e. the distance between the values 125 and 250 Hz is exactly equal to for example the distance between the values 2 kHz and 4 kHz. As in addition to octane values also intermediate values are used, the individual frequency values are not equidistantly spaced on the scale. The locking positions of the frequency slider should have the same distance from each other as the values on the frequency scale of the audiogram chart. Consequently, they are not equidistant either.

Furthermore, so-called speech audiometers are known which measure the intelligibility of words depending on the instantaneous sound level setting. By means of an audio carrier, for example a cassette recorder, a predetermined number of words (ten numbers and twenty words in the so-called Freiburg speech intelligibility test) are reproduced at a predetermined sound level. The person under test then attempts to repeat every word. The operator notes down the number of correctly repeated words and calculates therefrom the speech intelligibility in percent or the discrimination loss (= 100% minus speech intelligibility) and records the calculated value in a speech audiogram chart, which represents the intelligibility or the discrimination loss as a function of the sound level of speech. On one axis of such a speech audiogram the intelligibility (in percent) is plotted on a linear scale. Subsequently, the operator repeats this test with another test group with a corresponding number of words, but each at a different sound level of speech, again calculates the intelligibility and again records the intelligibility value determined at this sound level in the speech audiogram. This is comparatively time-consuming for the operator.

A known audiometer for combined speech and tone audiometry in which, for varying the sound level, the same amplifier is employed for the audio carrier and for the audio-frequency generator has the same disadvantage.

Furthermore, a speech audiometer is known in which a slider is provided which is movable in a direction perpendicular to that of the sound slever slider and which can be locked in equidistant locking positions, which slider is each time set one locking position further by the operator when the test word has been understood correctly. The position of this slider after reproduction of all the words of a group is consequently a measure of the intelligibility and can then be recorded directly by means of a marking templet, which intersects the marking templet which is connected to the level slider at right angles, so that the time-consuming calculation of the intelligibility values and errors in recording the speech audiogram are eliminated.

It is an object of the present invention to provide an audiometer for combined speech and tone audiometry which in both cases enables a simplified (semi-automatic) recording of the measurement values in the audiogram.

Starting from an audiometer of the type mentioned in the preamble this problem is solved in accordance with the invention in that for the purpose of speech audiometry a sound carrier, in particular a cassette recorder, is provided as well as a switch which selectively connects the output of the sound carrier (i.e. speech source) or the output of the audio frequency tone generator to the input of the amplifier. For the first slider a number of locking strips is provided corresponding to the number of tests to be carried out with the audiometer, and wherein an optional strip is each time in an operating position in which it determines the various locking positions of the first slider.

The invention is based on the recognition that the first slider, which is used for changing the frequencies in the case of tone audiometry, can be employed for determining the intelligibility in the case of speech audiometry by advancing the slide one position for each word which is understood. The problem that for speech audiometry, in contradistinction to tone audiometry, the slide should have equidistant locking positions is solved by the use of different locking strips for the various modes of operation.

A constructionally very simple embodiment is obtained when, in accordance with a modification of the invention, a spindle is rotatably journalled parallel to the direction of movement of the first slider, which spindle can be locked in a number of angular positions, and when for each of these angular positions a group of detents, preferably locking notches, is formed on the spindle parallel to the axis of rotation, one of which each time determines the locking position of the first slider.

In order to prevent a locking strip from being inadvertently brought into an operating position that is not suitable for a particular audiometer test, which is defined by the position of the switch between the audio frequency generator and the sound carrier, a modification of the invention ensures that a switch arrangement with a number of switch positions corresponding to the number of angular positions is coupled to the spindle. In addition an indicator, which is controlled by the switch arrangement and the switches, is provided which produces an optical or acoustic signal when the position of the switch and the angular position do not correspond.

In accordance with an even more efficient further modification of the invention the spindle is coupled to the switch for the various audiometer tests.

Figure 2:
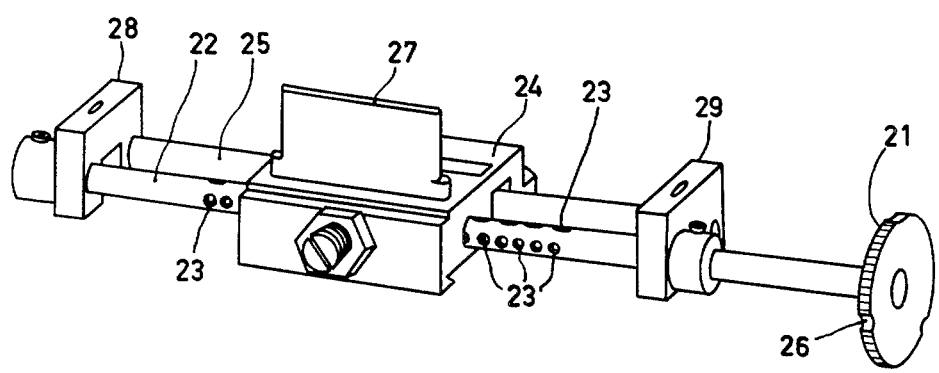

The invention and further advantages will be described in more detail with reference to the accompanying drawings, in which:

FIG. 1 shows a purely schematic block diagram of an audiometer in accordance with the invention together with the principal control elements, and FIG. 2 shows the spindle which can be locked in various angular positions.

The audiometer comprises a speech source or sound carrier 1, preferably a cassette recorder, and an audio frequency tone generator 2 whose frequency is variable in steps. A switch 3 enables either the output of the sound carrier 1, which is required for speech audiometry, or the output of the audio frequency generator 2, which is required for tone audiometry, to be connected to the input of an amplifier 4 whose gain is adjustable and to whose output a headphone can be connected.

Selection of the audio-frequency, switching between sound carrier and audio-frequency generator, i.e. between speech audiometry and tone audiometry, and the variation of the sound level (i.e. adjustment of the gain of the amplifier 4) are effected by controls which are situated on a control desk 5, which is only partly shown in FIG. 1. On the control desk 5 a first slider 6 is provided which is movable in a horizontal slot 7 and — as is indicated by the dash-dot line 8 — is coupled to the frequency control of the audio-frequency generator 2 so that by moving the frequency slider 6 the audio frequency can be varied in steps. A pointer-shaped marking templet 9 is connected to the slider 6, which templet has a central oblong slit 10.

On the control desk 5 a further slider 11 is provided which is movable in a slot 12 which is at right angles to the slot 7 and which at the same time varies the gain or the output power of the amplifier 4, as is indicated by the dash-dot line 13. Connected to the slider 11 is a transparent marking templet 14 in which two rows of holes 15 and 16 are formed. The measuring point determined by an audiometer test is defined by that hole of a row of holes which coincides with the slit 10 in the marking templet 9. The operator records this measuring point by means of a pencil through this hole on an audiogram 17 which is situated in a specific position underneath the marking templets.

Furthermore, two buttons 18 and 19 are provided on the control desk 5 which, as indicated by the dash-dot-line 20, enable the switch 3 to be changed over.

The mechanism for sliding the slider 6 is constructed so that a number of locking positions are obtained which — when the correct locking strip is in the operating position — corresponds to the number of test frequencies and whose distance corresponds to the spacing of the frequency values in the audiogram. When the locking strip for speech audiometry is in the operating position, a number of equidistant locking positions is obtained corresponding to the number of words per test group. The locking positions are defined by a spindle (or roller), not shown in FIG. 1, which by means of an actuating knob 21, which projects through an opening in the front plate of the control desk, can be set to various predetermined angular positions.

FIG. 2 shows such a spindle which is mounted in the control desk underneath the control panel and parallel to the direction of the slot 7. The spindle 22, which is adapted to three different modes of operation — for tone audiometry, for a speech test with ten words or sentences and for a speech test with twenty words or sentences — is rotatably journalled and can be locked in three angular positions which are preferably spaced 120° from each other. The spindle has three groups of axially extending locking notches 23 which are arranged on the circumference of the spindle in the same way as the angular positions in which the spindle can be locked; i.e. preferably 120° in the case of three angular positions or three modes of operation. The first group, which is operative in the case of tone audiometry, has a number of non-equidistant locking notches corresponding to the number of different test frequencies, whose distances from each other corresponds to the distances between the frequency values on the tone audiogram. The second group has ten equidistant locking notches for the speech test with ten words or sentences. Finally the third group of locking notches has twenty notches for the twenty words of the second speech test, which notches are also equidistantly spaced but at a distance which is half the distance between the locking notches of the second group. When the spindle is locked in any of the three angular positions, one of the three groups of locking notches is in the operative position. On a control member 21 which is mechanically coupled to the spindle marks 26 are provided which show the user which group of locking notches is in the operating position.

On the spindle 22 a sliding member 24 is movable in the longitudinal direction. A guide 25 is mounted parallel to the spindle and prevents this sliding member from being tilted. The sliding member is equipped with a resilient locking member, not shown, which bears against the spindle 22 at the level of the group of locking notches which is in the operating position and when the slider is moved engages with a locking notch of this group. The sliding member 24 is connected to a part 27 which projects through the slot 7 (FIG. 1) and on which in the assembled condition the slider 6 is mounted. The spindle is connected to the control panel of the control desk 5 by means of the blocks 28, 29.

The operation of the combined tone-speech audiometer in acoordance with the invention is essentially as follows:

By means of the push-buttons 18, 19 the operator indicates whether he wishes to conduct a speech test or a tone test. In the case of pure tone audiometry the switch 3 is then in the position shown in the drawing. The operator then actuates the control member 21 until the locking notches corresponding to the desired test are in the operating position, which is indicated by the mark 26. In the case of tone audiometry the threshold of hearing is then determined for each of the frequencies and is recorded on the audiogram 17 by means of the marking templets 14 and 9, the upper row of holes 15 in the marking templet 14 serving for recording the measuring points. The distance of the holes of this row from a vertical straight line then corresponds to the distance of the frequency values in the audiogram from this straight line or the distance between the individual locking positions.

If the operator now wishes to conduct a speech test he presses the push-button 19 so that the upper switch 3 assumes the switch position in FIG. 1, and a further switch, not shown, switches the cassette recorder 1 to the track on which the words corresponding to the relevant speech test are recorded. Simultaneously, he determines the locking positions corresponding to this test by means of the control 21 and moves the slide 6 to an initial position (to the extreme left). For each correctly understood word the operator then moves the slider one locking position to the right, and after a group of words has been played back the position of the marking templet 9 then is a measure of the intelligibility. The value found is then recorded via the row of holes 16 on the speech audiogram which must then be used instead of the tone audiogram used in FIG. 1. The measuring and recording process outlined is then repeated for different sound levels of speech. The lower row of holes 16 also has equidistant holes which are disposed on a straight line parallel to the slot 7, the number of holes corresponding to the number of words in a speech test. If a different speech test with twenty or ten words are to be performed, one row of twenty holes suffices. In the case of a ten-word speech test only every second hole is then disposed in the slit on the marking templet 9, because then only ten locking positions are available.

In order to prevent the possibility that, for example, in the case of a tone audiometer test which is preselected by means of the push-button 18 the locking positions for the speech audiometer test remain in the operating position, the spindle 22 may be provided with a three-position rotary switch, not shown, which together with the push-buttons 18, 19 and as the case may be a further push-button (if two different speech tests are provided) controls an alarm device, not shown, which provides an optical or acoustic warning signal when the position of the switch and the angular position of the spindle do not correspond. It is even more effective — as is symbolically shown by the dash-dot line 30 in FIG. 1 — to couple the spindle 22 and the switch 3, so that when the spindle is rotated the switch is automatically set to the correct position. In this case the push-buttons may be dispensed with. The audiometer may also be designed so that the angular position of the spindle 22 is adjustable by means of the push-buttons 18, 19 for selecting the relevant audiometer test. In that case the button 21 may be dispensed with.

What is claimed is:

1. An audiometer comprising, an audio-frequency tone generator whose frequency is variable in steps by means of a first slider which locks in different locking positions, an amplifier whose output signal is variable by means of a second slider which is movable perpendicularly to the direction of movement of the first slider, first and second marking templets connected to said first and second sliders, respectively, each marking templet extending substantially perpendicularly to the direction of movement of its respective slider and parallel to the direction of movement of the other slider, a speech source including a sound carrier, a switch for selectively connecting the output of the sound carrier or the audio-frequency tone generator to the input of the amplifier, and means coupled to the first slider comprising a number of locking strips corresponding to the number of tests to be performed with the audiometer so that for each test a selected strip is in an operating position in which it determines the various locking positions of the first slider.

2. An audiometer as claimed in claim 1 wherein the second slider is coupled to the amplifier so as to vary the amplifier gain and the first slider is coupled through a slot in a control panel to a rotatable spindle located on the opposite side of said panel, said spindle comprising first and second axially extending rows of locking notches which determine the locking positions of the first slider, said spindle being adapted to be locked in first and second angular positions corresponding to said first and second rows of notches which in turn correspond to tone and speech audiometry tests, respectively.

3. An audiometer as claimed in claim 1 wherein the means comprising a number of locking strips comprises a rotatable spindle extending parallel to the direction of movement of the first slider and comprising first and second axially extending rows of locking notches which determine the locking positions of the first slider, said spindle being adapted to be locked in three angular positions spaced 120° apart which correspond to the tests to be performed with the audiometer.

4. An audiometer comprising, an audio-frequency tone generator whose frequency is variable in steps, a first slider which can be locked in different locking positions and coupled to the tone generator to vary its frequency, an amplifier, a second slider movable in a direction perpendicular to the direction of movement of the first slider and coupled to the amplifier so as to vary the level of the amplifier output signal, first and second marking templets connected to said first and second sliders, respectively, with each marking templet extending perpendicular to the direction of movement of its respective slider and parallel to the direction of movement of the other slider, a source of speech including a sound carrier, a switch for selectively connecting the output of the sound carrier or the audio-frequency tone generator to the input of the amplifier, a rotatably journalled spindle extending parallel to the direction of movement of the first slider and arranged to be locked in a plurality of angular positions, for each of said angular positions a group of detents being formed on the spindle which extend parallel to the axis of rotation, and means for coupling the spindle to the first slider so that each detent determines a locking position of said first slider.

5. An audiometer as claimed in claim 4 further comprising means for coupling the spindle to said switch so that rotation of the spindle to each of said angular positions automatically sets the switch to the correct test position.

6. An audiometer as claimed in claim 4 further comprising a switch arrangement coupled to the spindle and having a number of switch positions corresponding to the number of angular positions of the spindle, and an indicator controlled by the switch arrangement and the switch for producing a warning signal when the position of the switch and the angular position of the spindle do not correspond.

7. An audiometer as claimed in claim 4 wherein the marking templet which is connected to the second slider is transparent and is provided with two rows of holes, of which one row comprises equidistantly arranged holes which are disposed in a straight line perpendicular to the direction of movement of the second slider, and the other row of holes being arranged so that the distance of a hole from a straight line which is parallel to the direction of movement of the second slider corresponds to the distance between the frequency values in a audiogram.

8. An audiometer as claimed in claim 4 wherein said spindle comprises at least two groups of axially extending detents the first of which comprises a row of variably spaced notches and the second of which comprises a row of equally spaced notches.

* * * * *